United States Patent
Lynch et al.

(10) Patent No.: US 7,083,597 B2
(45) Date of Patent: Aug. 1, 2006

(54) PIVOTING JOINT INFUSION SYSTEM WITH SEAL

(75) Inventors: George R. Lynch, Coppell, TX (US); Allen E. Brandenburg, Dripping Springs, TX (US); Andrew Nelson, Dallas, TX (US); Gilles Petitjean, Issoudun (FR)

(73) Assignee: Applied Diabetes Research, Inc., Carrollton, TX (US)

( * ) Notice: Subject to any disclaimer, the term of this patent is extended or adjusted under 35 U.S.C. 154(b) by 576 days.

(21) Appl. No.: 10/463,629

(22) Filed: Jun. 17, 2003

(65) Prior Publication Data

US 2004/0044306 A1    Mar. 4, 2004

Related U.S. Application Data

(63) Continuation-in-part of application No. 09/896,149, filed on Jun. 29, 2001, now Pat. No. 6,579,267.

(60) Provisional application No. 60/259,971, filed on Jan. 5, 2001.

(51) Int. Cl.
    *A61M 5/32* (2006.01)
(52) U.S. Cl. ......................... 604/174
(58) Field of Classification Search ............. 604/174, 604/178, 179, 180; 128/DIG. 6, DIG. 26
    See application file for complete search history.

(56) References Cited

U.S. PATENT DOCUMENTS

| | | |
|---|---|---|
| 3,547,119 A | 12/1970 | Niles et al. |
| 3,739,778 A | 6/1973 | Monestere, Jr. et al. |
| 3,996,923 A | 12/1976 | Guerra |
| 4,106,491 A | 8/1978 | Guerra |
| 4,126,133 A | 11/1978 | Schwartz |
| 4,258,940 A | 3/1981 | Fudge |
| 4,311,136 A | 1/1982 | Weikl et al. |
| 4,311,137 A | 1/1982 | Gerard |
| 4,418,944 A | 12/1983 | Haines et al. |
| 4,430,081 A | 2/1984 | Timmermans |
| 4,531,937 A | 7/1985 | Yates |
| 4,581,014 A * | 4/1986 | Millerd et al. ............. 604/80 |
| 4,645,495 A | 2/1987 | Vaillancourt |
| 4,755,173 A | 7/1988 | Konopka et al. |
| 5,019,054 A | 5/1991 | Clement et al. |
| 5,098,394 A | 3/1992 | Luther |
| 5,176,662 A | 1/1993 | Bartholomew et al. |
| 5,257,980 A | 11/1993 | Van Antwerp et al. |
| 5,281,206 A | 1/1994 | Lopez |
| 5,300,045 A | 4/1994 | Plassche, Jr. |
| 5,330,450 A | 7/1994 | Lopez |
| 5,427,145 A | 6/1995 | Grabenkort |
| 5,545,143 A | 8/1996 | Fischell |
| 5,613,663 A | 3/1997 | Schmidt et al. |

(Continued)

FOREIGN PATENT DOCUMENTS

FR    2578746 A1    9/1986

*Primary Examiner*—Eduardo C. Robert
*Assistant Examiner*—Anu Ramana
(74) *Attorney, Agent, or Firm*—Jackson Walker, LLP

(57) ABSTRACT

An infusion system for delivery of therapeutic fluids from a remote source into a patient's body. The system has an infusion assembly, a rotating pivot joint member, a fluid connector assembly, and a sealing assembly retained within the infusion assembly between the housing of the infusion assembly and the rotating pivot joint member. The seal reduces leakage of fluids. The rotating joint may be pivoted to three distinct positions to allow for emplacement on the patient, delivery of the therapeutic fluid to the patient, and protected, sealed closure of the fluid channels to avoid patient fluid backflow.

8 Claims, 3 Drawing Sheets

U.S. PATENT DOCUMENTS

| | | |
|---|---|---|
| 5,814,020 A | 9/1998 | Gross |
| 5,848,990 A | 12/1998 | Cirelli et al. |
| 5,851,197 A | 12/1998 | Marano et al. |
| D404,482 S | 1/1999 | Falk et al. |
| 5,858,001 A | 1/1999 | Tsals et al. |
| 5,968,011 A | 10/1999 | Larsen et al. |
| 5,980,506 A | 11/1999 | Mathiasen |
| 6,017,328 A | 1/2000 | Fischell et al. |
| 6,056,718 A | 5/2000 | Funderburk et al. |
| 6,093,172 A | 7/2000 | Funderburk et al. |
| 6,095,997 A | 8/2000 | French et al. |
| 6,186,982 B1 | 2/2001 | Gross et al. |
| 6,213,973 B1 | 4/2001 | Eliasen et al. |
| 6,302,866 B1 | 10/2001 | Marggi |
| 6,355,021 B1 | 3/2002 | Nielsen et al. |
| 6,419,699 B1 | 7/2002 | Schuessler |
| 6,736,797 B1 * | 5/2004 | Larsen et al. .......... 604/167.05 |
| 2002/0045867 A1 | 4/2002 | Nielsen et al. |
| 2002/0123724 A1 | 9/2002 | Douglas et al. |

\* cited by examiner

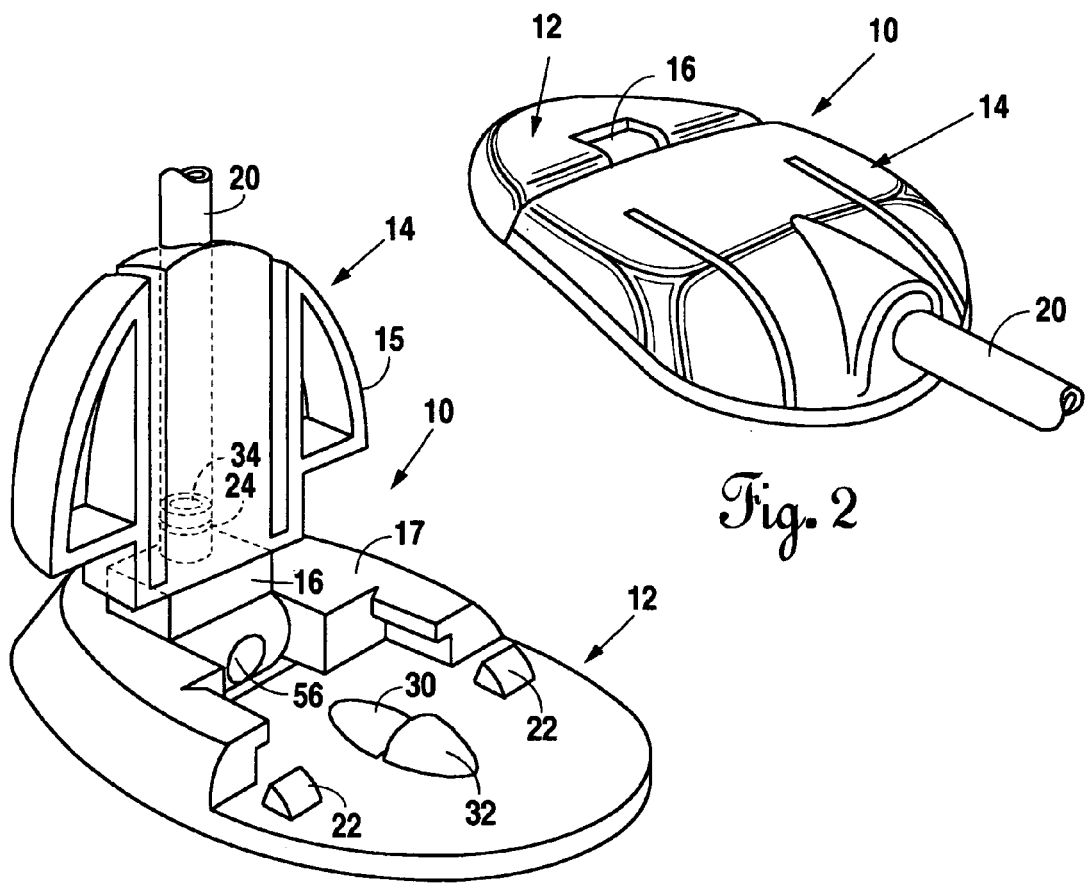
Fig. 2
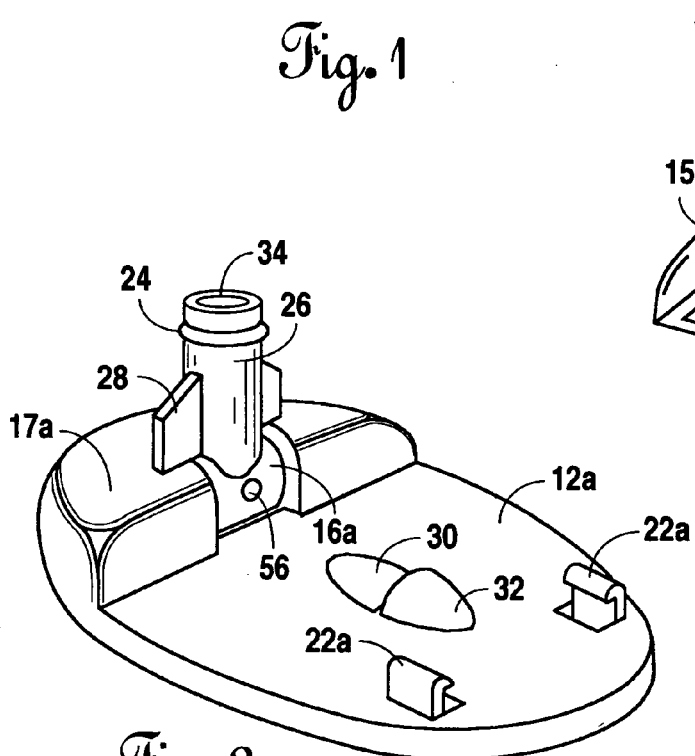
Fig. 1
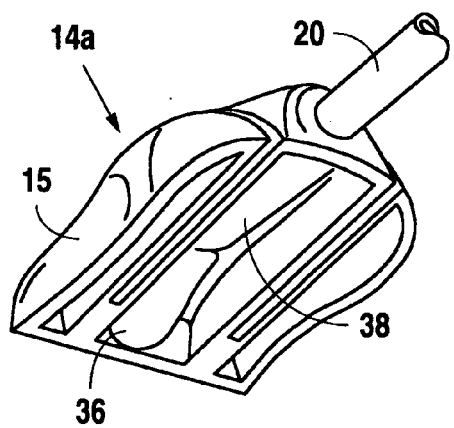
Fig. 4
Fig. 3

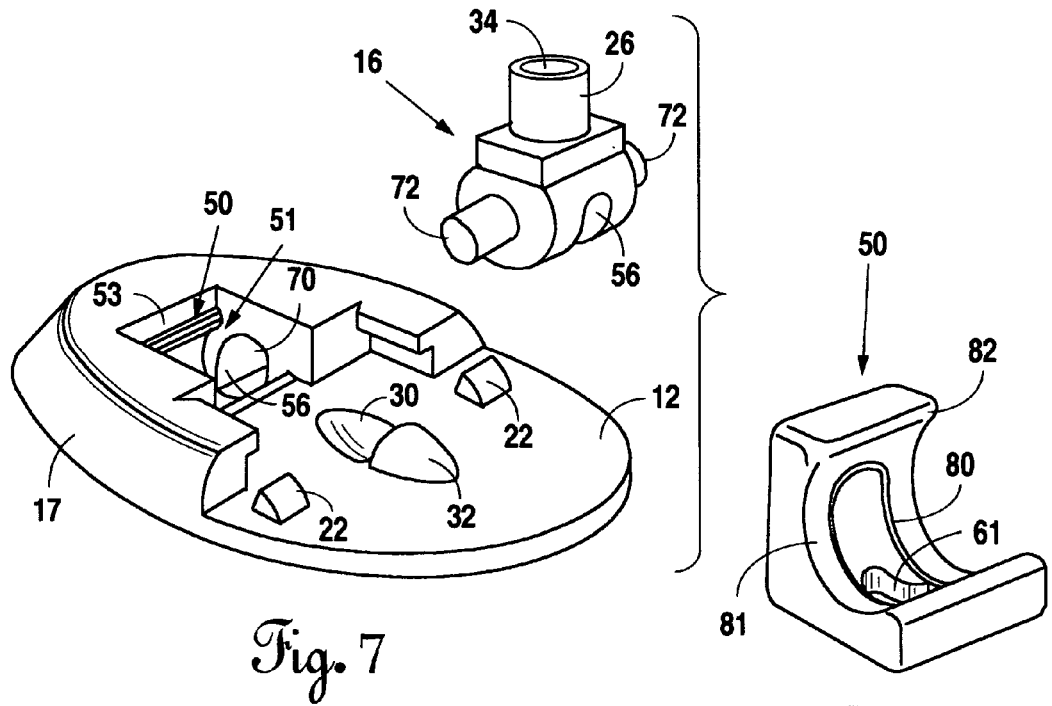
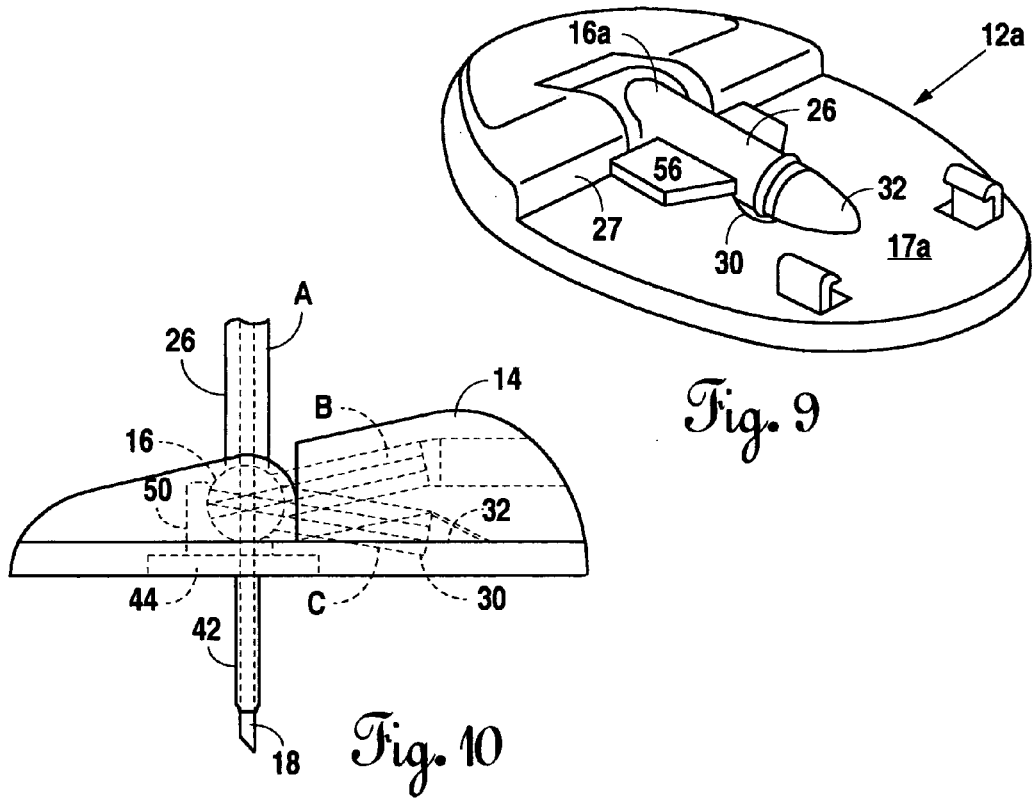

PIVOTING JOINT INFUSION SYSTEM WITH SEAL

This application is a continuation-in-part application of U.S. patent application Ser. No. 09/896,149, filed Jun. 29, 2001, now U.S. Pat. No. 6,579,267, issued Jun. 17, 2003, which claims priority to U.S. Provisional Application No. 60/259,971, filed Jan. 5, 2001, all of which are incorporated herein by reference for all purposes.

FIELD OF THE INVENTION

The present invention relates to an improved system for subcutaneous delivery of fluid to a patient. More particularly, the present invention relates to an infusion system having an improved sealing subsystem cooperating with a rotating pivot joint member that delivers the fluid from a remote source to a delivery cannula of the main infusion assembly of the system.

BACKGROUND OF THE INVENTION

Prior art infusion sets or systems provide numerous ways for engaging a fluid connector to a base to deliver a therapeutic fluid subcutaneously to a patient. Most of these prior art systems are plagued with leaking connections and inefficient ways to allow the patient to disconnect the fluid connector from the base without a backflow of fluid from the patient through the base and back into the environment.

The present invention provides an improved sealing subsystem incorporated into a pivoting or rotating "ball" joint that moves from an emplacement position to an infusion or delivery position to a disconnected, protected, closed position.

BRIEF DESCRIPTION OF THE DRAWINGS

FIG. 1 illustrates a perspective view of the present invention system with the fluid connector attached to the rotating pivot member in a vertical, non-delivery position.

FIG. 2 shows the fluid connection moved to an operating, infusion or delivery position and locked in engagement with the base unit.

FIG. 3 shows the base unit of the present invention with the rotating pivot member in the vertical position to accept an emplacement needle assembly.

FIG. 4 is a bottom perspective view of the fluid connector of the present invention with a fluid delivery tube attached thereto.

FIG. 7 is an exploded perspective view of the base unit of the present invention showing the seal assembly and the rotating pivot member.

FIG. 8 is a detailed perspective view of the seal assembly of the present invention.

FIG. 9 illustrates a perspective view of the base assembly and the rotating pivot member of the present invention rotated to a protected closed position to prevent backflow of patient fluids.

FIG. 10 shows three distinct positions of the rotating or pivoting member of the present invention, namely, the emplacement position, the infusion position, and the protected, closed position.

DETAILED DESCRIPTION OF THE PREFERRED EMBODIMENT OF THE PRESENT INVENTION

Figure 5:
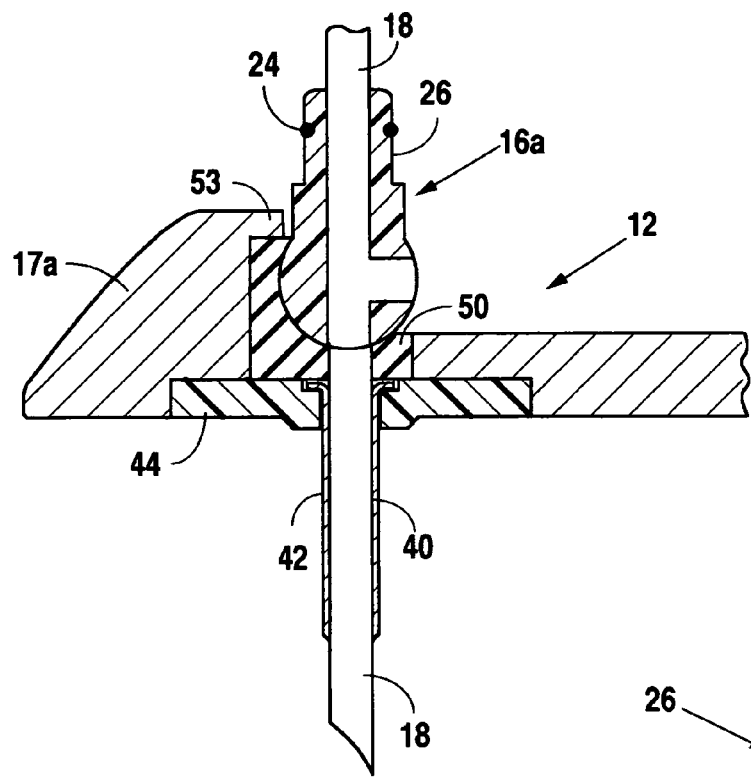
FIG. 5 illustrates a partial cross sectional side elevation plan view of the present invention in a first emplacement position.

FIG. 1 is a perspective view of the infusion system 10 of the present invention. In FIG. 1, the main infusion unit 12 is shown with the fluid connector assembly 14 attached to the rotating pivot joint member 16. The joint member 16 is rotatably attached to the housing 17 of unit 12. The emplacement needle 18 (FIG. 5) has been withdrawn and the connector assembly is still in an upright or vertical position. Therapeutic fluid from a remote source (not shown but well known in the art) such as a wall or rack hung bottle or plastic fluid bag may be delivered through delivery tube 20 to the connector assembly 14 and into the patient. However, the preferred procedure is for the needle to be withdrawn and the joint member 16 slightly rotated downwardly to misalign the emplacement channel 54 (FIG. 5A) and the injection channel 40. This will prevent or significantly avoid a backflow of patient fluids as will be discussed below. The connector assembly 14 is then attached to the joint member 16 and the rotating joint member and the connector assembly 14 are to be rotated about joint member 16 to the horizontal delivery or infusion position shown in FIG. 2. In FIG. 2, the fluid connector 14 has rotated about joint 16 and has locked onto the locking tabs 22 (FIG. 1) of the main infusion unit 12 and is thereby held securely in place.

FIG. 3 shows a slightly modified main infusion unit 12a having a pivot joint member 16a with an 0-ring seal 24 on neck section 26 of the joint. Neck 26 has opposing wings 28 which serve to ensure an aligned rotation of the joint 16a about the housing 17a. The wings further function to ensure proper alignment of the connector assembly 14a to the main infusion unit 12a. FIG. 9 additionally shows how wings 28 hold the neck 26 in a third distinct position. FIG. 3 also illustrates a recess section 30 and cover 32 in housing 17a. As will be described below, the recess 30 accepts the top section of neck 26 in a third rotated position of joint 16a and cover 32 shields, protects, and seals the central fluid channel 34 in the joint member 16a when the fluid connector has been removed from the rotating pivot joint member 16a.

FIG. 4 illustrates in a perspective view the underside or bottom side of the fluid connector 14a which attaches at a near end 36 to the rotating pivot joint member. It should be noted in FIG. 4 that the fluid delivery channel 38 in connector 14a has a slight approach angle variation as will be described in more detail in the discussion of FIG. 10.

The structural arrangement or relationship of the joint member 16a to housing 17a is seen in the partial cross sectional view of FIG. 5. FIG. 5 shows the joint 16a in a first emplacement position with an emplacement needle 18 extending through the rotating joint 16a, through the injection channel 40 of cannula 42, and subcutaneously piercing the skin of the patient. A retainer plate 44 holds the cannula 18 within the housing 17a. The emplacement of the needle and how the main infusion unit may be affixed to the patient are well understood as described in U.S. Pat. No. 6,579,267. Also shown in FIG. 5 is the placement and retention of sealing assembly 50 within housing 17. FIG. 8 shows the sealing assembly in greater detail.

Figure 5A:
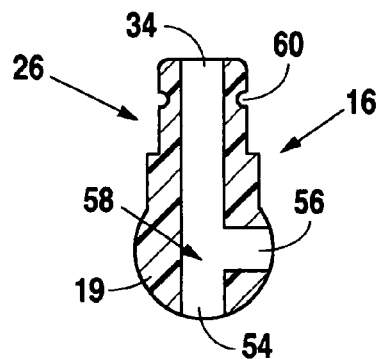

The rotating pivot joint member 16a is shown in a side elevational cross sectional view in FIG. 5A. Central fluid channel 34, needle emplacement channel 54, and fluid infusion channel 56 intersect in a central portion 58 of the joint 16a. Grooves 60 are provided for 0-ring seals in the neck section.

Figure 6:
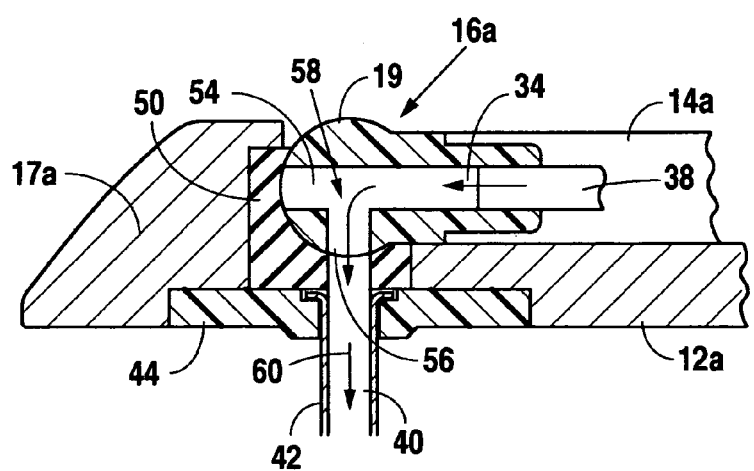
FIG. 6 shows the pivot member and base unit of FIG. 5 with the emplacement needle withdrawn and the rotating pivot member rotated to a second infusion or delivery position.

FIG. 6 shows the pivot member or joint 16a with the emplacement needle withdrawn and fluid connector assembly 14a attached. The joint 16a is rotated to an infusion or delivery position with the infusion channel 56 aligned with the injection channel 40 in cannula 42. Thus, therapeutic fluid 60 from the remote source flows through fluid delivery channel 38 in connector assembly 14a into central fluid channel 34, into infusion channel 56 through cannula injection channel 40 into the patient. As would be understood by one of skill in the art, the connector assembly 14a is secured to the main infusion unit 12a by the locking tabs 22 urging against the body 15 of the connector assembly.

In FIG. 7 an exploded perspective illustration is provided of pivot joint member 16, housing 17, sealing assembly 50, and rotating pivot joint member receiving chamber 51. The joint 16 has axial rotation journals or ears 72 which engage in slots 70 in the receiving chamber 51. The sealing assembly also fits snugly between the housing 17 and the joint 16 when the system is fully assembled. Turning to FIGS. 5 and 6 it may be seen that elastomeric seal 50 is urged beneath overhanging ledge 53 of housing 17 and is thereby further held in position. When the joint 16 is rotatably secured in the chamber 51, the seal 50 provides a sealing surface for the joint body 19 to sealingly rotate upon. In FIG. 8, the L-shaped seal assembly 50 has an orifice 61 to allow the needle or fluid to pass through. A raised rib 80 along the inner surface 81 of the seal may be used to provide an additionally tight seal. It should be understood that the use of various cooperating materials may be used in the construction of the seal 50 and the joint body 19. A hard-to-soft surface interface may be employed. The seal may be softer than the joint or vice versa. Two hard surfaces with cooperating coefficients of friction may be employed.

A protected, closed, and sealed third position of the rotating pivot joint member 16a is shown in FIG. 9. When the patient removes the connector assembly 14 or 14a from the pivot joint 16 or 16a, the alignment of the injection channel and the infusion channel in the joint would allow patient fluids to flow back through the infusion assembly and leak or flow into the environment. However, a unique feature of the present invention allows the user to rotate the pivot joint 16a downwardly to a third distinct position placing the neck 26 and central fluid channel 34 into recess 30 with cover 32 sealing off the open channel 34. Thus, no patient fluids backflow through the system. FIG. 9 also illustrates that alignment wings 28 also function to stop the downward rotation of the joint 16a; and, because they rub or slide tightly along housing shoulder 27 of the main infusion assembly 12a, the neck 26 is retained in the recess during the user's movement.

The distinct positions of the rotating "ball" pivot joint member 16 are illustrated in FIG. 10. In position A, the emplacement needle may be guided through the appropriate channels in the joint to allow the main infusion unit 12 to be attached to the patient. In position B, the needle has been removed and the fluid connector assembly 14 attached to the joint 16. The fluid channels in the connector assembly and the joint are aligned to allow for the therapeutic fluid to flow from the remote source through the delivery tube, through the joint and cannula channels to the patient. In position C, the fluid connector assembly 14 has been removed and the joint rotated further downwardly to rest in recess 30 with cover 32 sealing the fluid channel 34. Additionally, the further rotation of the joint misaligns the infusion channel 56 of the joint from the injection channel 40 of the cannula thereby further sealing off the backflow of any patient fluids through the system to the environment.

It may be seen in FIG. 10 that the sealing assembly 50 directly engages over 90° of the surface of the pivot joint 16 in any one of the distinct positions; but, because of the rotatability of the joint, over 270° of the ball joint surface is sealingly urged against the seal assembly 50. This feature provides for a more efficient sealing of the channels in the joint thereby reducing leakage problems associated with the prior art.

Although the invention has been described with reference to a specific embodiment, this description is not meant to be construed in a limiting sense. On the contrary, various modifications of the disclosed embodiments will become apparent to those skilled in the art upon reference to the description of the invention. It is therefore contemplated that the appended claims will cover such modifications, alternatives, and equivalents that fall within the true spirit and scope of the invention.

The invention claimed:

1. An infusion system for delivery of a therapeutic fluid from a remote source into a patient's body comprising.
   a main infusion unit having a housing, a cannula with an injection channel, said cannula attached at an underside of said main infusion unit, a first fluid channel in communication with said cannula, and a rotating joint member receiving chamber;
   a rotating joint member having a central fluid channel, a needle emplacement channel, and a fluid infusion channel, all of said channels intersecting within a central portion of said rotating joint member, said rotating member adapted to be received within and rotatable within said chamber;
   a fluid connector assembly having a fluid delivery channel, said fluid connector assembly attachable at an end of said rotating joint member such that said fluid delivery channel aligns with and is in communication with said central fluid channel of said rotating joint member, said fluid connector assembly attachable at a remote end to a delivery tube attached to said remote source of said therapeutic fluid;
   a sealing assembly retained within said rotating joint member receiving chamber between said rotating joint member and said main infusion unit housing;
   said rotating joint member rotatable from a first vertical emplacement position whereby an emplacement needle may be extended through said emplacement channel of said rotating joint member and through said injection channel of said cannula to subcutaneously pierce said patient to a second delivery position after said emplacement needle has been withdrawn from said patient and said fluid connector assembly has been attached at said near end to said rotating joint member, said second delivery position aligning said fluid infusion channel with said injection channel of said cannula to deliver said therapeutic fluid to said patient.

2. The system of claim 1 wherein said main infusion unit further comprises a recess in said housing to receive and retain a neck portion of said rotating joint member when said rotating joint member is rotated to a third position; and a cover on said housing to protect and cover an opening to said central fluid channel in said rotating joint member when said rotating joint member is rotated to said third position.

3. The system of claim 2 wherein said neck portion of said rotating joint member further comprises a seal ring.

4. The system of claim 2 wherein said rotating joint member further comprises opposing alignment and retention wings, said wings in sliding contact with a shoulder portion of said main infusion unit housing.

5. The system of claim 1 wherein said sealing assembly further comprises a L-shaped elastomeric seal member having a raised rim portion along a surface abutting said rotating joint member when said rotating joint member is retained in said rotating joint member receiving chamber.

6. The system of claim 5 wherein said seal member contacts and seals along more than 90° of the outer rotation surface of said rotating joint member.

7. The system of claim 1 wherein said rotating joint member further comprises axial rotation journals adapted to be received and rotatably retained in slots in said receiving chamber.

8. The system of claim 1 wherein said sealing assembly is retained in said receiving chamber by an overhanging ledge in said main infusion unit housing.

* * * * *